(12) United States Patent
Roberts

(10) Patent No.: US 10,089,714 B2
(45) Date of Patent: *Oct. 2, 2018

(54) PERSONALIZED SCALING OF GRAPHICAL INDICATORS

(71) Applicant: Fitbit, Inc., San Francisco, CA (US)

(72) Inventor: Timothy Roberts, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 15/189,245

(22) Filed: Jun. 22, 2016

(65) Prior Publication Data
US 2016/0307295 A1    Oct. 20, 2016

Related U.S. Application Data

(63) Continuation of application No. 14/250,635, filed on Apr. 11, 2014, now Pat. No. 9,449,365.

(51) Int. Cl.
*G09G 5/00* (2006.01)
*G06T 3/40* (2006.01)
(Continued)

(52) U.S. Cl.
CPC .............. *G06T 3/40* (2013.01); *A61B 5/0059* (2013.01); *A61B 5/02438* (2013.01); *A61B 5/1112* (2013.01); *A61B 5/1118* (2013.01); *A61B 5/14542* (2013.01); *A61B 5/681* (2013.01); *A61B 5/743* (2013.01); *A61B 5/7425* (2013.01); *A61B 5/7435* (2013.01); *G06T 11/206* (2013.01); *G08B 21/24* (2013.01);
(Continued)

(58) Field of Classification Search
None
See application file for complete search history.

(56) References Cited

U.S. PATENT DOCUMENTS 2,717,736 A    9/1955    Schlesinger
2,883,255 A    4/1959    Anderson
(Continued)

FOREIGN PATENT DOCUMENTS

WO    2008038141    4/2008
WO    2009042965    4/2009

OTHER PUBLICATIONS

"Forerunner 301 Personal Trainer Owner's Manual", Feb. 2006, Garmin Ltd. or its subsidiaries, Part No. 190-00370-00 Rev. F. 65 pgs.
(Continued)

*Primary Examiner* — M Good Johnson
(74) *Attorney, Agent, or Firm* — Weaver Austin Villeneuve & Sampson LLP

(57) ABSTRACT

Some aspects relate to reception from a user, via a sensor, first data indicative of activity of the user, determination of one or more values of a metric based on the first data, determination of a display scale based on the one or more values, reception from the user, via the sensor, second data indicative of activity of the user over a time interval, determination of a second value of the metric based on the second data, generation of a first graphical indicator representing the second value based on the display scale and the second value, and display of the first graphical indicator on a display.

40 Claims, 13 Drawing Sheets

(51) Int. Cl.
　　*G06T 11/20*　　(2006.01)
　　*A61B 5/024*　　(2006.01)
　　*A61B 5/11*　　(2006.01)
　　*A61B 5/145*　　(2006.01)
　　*G08B 21/24*　　(2006.01)
　　*A61B 5/00*　　(2006.01)

(52) U.S. Cl.
　　CPC .............. *A61B 5/0002* (2013.01); *A61B 5/742* (2013.01); *A61B 2562/0219* (2013.01); *A61B 2562/0223* (2013.01); *A61B 2562/0257* (2013.01); *G06T 2210/41* (2013.01)

(56) References Cited

U.S. PATENT DOCUMENTS

| | | | |
|---|---|---|---|
| 3,163,856 | A | 12/1964 | Kirby |
| 3,250,270 | A | 5/1966 | Bloom |
| 3,918,658 | A | 11/1975 | Beller |
| 4,192,000 | A | 3/1980 | Lipsey |
| 4,244,020 | A | 1/1981 | Ratcliff |
| 4,281,663 | A | 8/1981 | Pringle |
| 4,284,849 | A | 8/1981 | Anderson et al. |
| 4,312,358 | A | 1/1982 | Barney |
| 4,367,752 | A | 1/1983 | Jimenez et al. |
| 4,390,922 | A | 6/1983 | Pelliccia |
| 4,407,295 | A | 10/1983 | Steuer et al. |
| 4,575,804 | A | 3/1986 | Ratcliff |
| 4,578,769 | A | 3/1986 | Frederick |
| 4,617,525 | A | 10/1986 | Lloyd |
| 4,887,249 | A | 12/1989 | Thinesen |
| 4,962,469 | A | 10/1990 | Ono et al. |
| 4,977,509 | A | 12/1990 | Pitchford et al. |
| 5,058,427 | A | 10/1991 | Brandl |
| 5,224,059 | A | 6/1993 | Nitta et al. |
| 5,295,085 | A | 3/1994 | Hoffacker |
| 5,323,650 | A | 6/1994 | Fullen et al. |
| 5,446,705 | A | 8/1995 | Haas et al. |
| 5,456,648 | A | 10/1995 | Edinburg et al. |
| 5,583,776 | A | 12/1996 | Levi et al. |
| 5,583,830 | A | 12/1996 | Okuyama |
| 5,671,162 | A | 9/1997 | Werbin |
| 5,704,350 | A | 1/1998 | Williams, III |
| 5,724,265 | A | 3/1998 | Hutchings |
| 5,737,246 | A | 4/1998 | Furukawa et al. |
| 5,788,655 | A | 8/1998 | Yoshimura et al. |
| 5,890,997 | A | 3/1999 | Diaz et al. |
| 5,891,042 | A | 4/1999 | Sham et al. |
| 5,894,311 | A | 4/1999 | Jackson |
| 5,899,963 | A | 5/1999 | Hutchings |
| 5,908,396 | A | 6/1999 | Hayakawa et al. |
| 5,947,868 | A | 9/1999 | Dugan |
| 5,955,667 | A | 9/1999 | Fyfe |
| 5,976,083 | A | 11/1999 | Richardson et al. |
| 6,018,705 | A | 1/2000 | Gaudet et al. |
| 6,077,193 | A | 6/2000 | Buhler et al. |
| 6,085,248 | A | 7/2000 | Sambamurthy et al. |
| 6,129,686 | A | 10/2000 | Friedman |
| 6,145,389 | A | 11/2000 | Ebeling et al. |
| 6,183,425 | B1 | 2/2001 | Whalen et al. |
| 6,213,872 | B1 | 4/2001 | Harada et al. |
| 6,241,684 | B1 | 6/2001 | Amana et al. |
| 6,269,054 | B1 | 7/2001 | Truini |
| 6,287,262 | B1 | 9/2001 | Amana et al. |
| 6,301,964 | B1 | 10/2001 | Fyfe et al. |
| 6,302,789 | B2 | 10/2001 | Harada et al. |
| 6,305,221 | B1 | 10/2001 | Hutchings |
| 6,309,360 | B1 | 10/2001 | Mault |
| 6,469,639 | B2 | 10/2002 | Tanenhaus et al. |
| 6,478,736 | B1 | 11/2002 | Mault |
| 6,513,381 | B2 | 2/2003 | Fyfe et al. |
| 6,513,532 | B2 | 2/2003 | Mault et al. |
| 6,525,997 | B1 | 2/2003 | Narayanaswami et al. |
| 6,527,711 | B1 | 3/2003 | Stivoric et al. |
| 6,529,827 | B1 | 3/2003 | Beason et al. |
| 6,556,222 | B1 | 4/2003 | Narayanaswami |
| 6,561,951 | B2 | 5/2003 | Cannon et al. |
| 6,571,200 | B1 | 5/2003 | Mault |
| 6,583,369 | B2 | 6/2003 | Montagnino et al. |
| 6,585,622 | B1 | 7/2003 | Shum et al. |
| 6,601,988 | B2 | 8/2003 | Molander |
| 6,607,493 | B2 | 8/2003 | Song |
| 6,620,078 | B2 | 9/2003 | Pfeffer |
| 6,678,629 | B2 | 1/2004 | Tsuji |
| 6,699,188 | B2 | 3/2004 | Wessel |
| 6,704,016 | B1 | 3/2004 | Oliver et al. |
| 6,720,860 | B1 | 4/2004 | Narayanaswami |
| 6,761,064 | B2 | 7/2004 | Tsuji |
| 6,790,178 | B1 | 9/2004 | Mault et al. |
| 6,808,473 | B2 | 10/2004 | Hisano et al. |
| 6,811,516 | B1 | 11/2004 | Dugan |
| 6,813,582 | B2 | 11/2004 | Levi et al. |
| 6,813,931 | B2 | 11/2004 | Yadav et al. |
| 6,856,938 | B2 | 2/2005 | Kurtz |
| 7,006,856 | B2 | 2/2006 | Baker et al. |
| 7,035,170 | B2 * | 4/2006 | Narayanaswami .. G04G 9/0082 368/10 |
| 7,062,225 | B2 | 6/2006 | White |
| 7,113,450 | B2 | 9/2006 | Plancon et al. |
| 7,162,368 | B2 | 1/2007 | Levi et al. |
| 7,167,743 | B2 | 1/2007 | Heruth et al. |
| 7,171,331 | B2 | 1/2007 | Vock et al. |
| 7,200,517 | B2 | 4/2007 | Darley et al. |
| 7,246,033 | B1 | 7/2007 | Kudo |
| 7,261,690 | B2 | 8/2007 | Teller et al. |
| 7,272,982 | B2 | 9/2007 | Neuhauser et al. |
| 7,278,966 | B2 | 10/2007 | Hjelt et al. |
| 7,373,820 | B1 | 5/2008 | James |
| 7,443,292 | B2 | 10/2008 | Jensen et al. |
| 7,457,724 | B2 | 11/2008 | Vock et al. |
| 7,467,060 | B2 | 12/2008 | Kulach et al. |
| 7,505,865 | B2 | 3/2009 | Ohkubo et al. |
| 7,533,326 | B2 | 5/2009 | Chambers |
| 7,559,877 | B2 | 7/2009 | Parks et al. |
| 7,587,237 | B2 | 9/2009 | Korzinov et al. |
| 7,623,415 | B2 | 11/2009 | Raeber et al. |
| 7,653,508 | B1 | 1/2010 | Kahn et al. |
| 7,676,332 | B2 * | 3/2010 | Damen ................... A61B 5/222 600/300 |
| 7,690,556 | B1 | 4/2010 | Kahn et al. |
| 7,713,172 | B2 | 5/2010 | Shin et al. |
| 7,717,866 | B2 | 5/2010 | Damen |
| 7,738,320 | B2 | 6/2010 | Taha |
| 7,774,156 | B2 | 8/2010 | Niva et al. |
| 7,789,802 | B2 | 9/2010 | Lee et al. |
| 7,881,802 | B2 | 2/2011 | Quiles et al. |
| 7,927,253 | B2 | 4/2011 | Vincent et al. |
| 7,940,604 | B2 | 5/2011 | Inoue et al. |
| 7,959,539 | B2 | 6/2011 | Takeishi et al. |
| 7,983,876 | B2 | 7/2011 | Vock et al. |
| 8,028,443 | B2 | 10/2011 | Case, Jr. |
| 8,055,469 | B2 | 11/2011 | Kulach et al. |
| 8,099,318 | B2 | 1/2012 | Moukas et al. |
| 8,177,260 | B2 | 5/2012 | Trapper et al. |
| 8,180,591 | B2 | 5/2012 | Yuen et al. |
| 8,180,592 | B2 | 5/2012 | Yuen et al. |
| 8,257,228 | B2 | 9/2012 | Quatrochi et al. |
| 8,311,769 | B2 | 11/2012 | Yuen et al. |
| 8,311,770 | B2 | 11/2012 | Yuen et al. |
| 8,350,856 | B1 | 1/2013 | Nazir et al. |
| 8,386,008 | B2 | 2/2013 | Yuen et al. |
| 8,437,980 | B2 | 5/2013 | Yuen et al. |
| 8,463,576 | B2 | 6/2013 | Yuen et al. |
| 8,463,577 | B2 | 6/2013 | Yuen et al. |
| 8,475,367 | B1 | 7/2013 | Yuen et al. |
| 8,543,185 | B2 | 9/2013 | Yuen et al. |
| 8,543,351 | B2 | 9/2013 | Yuen et al. |
| 8,548,770 | B2 | 10/2013 | Yuen et al. |
| 8,583,402 | B2 | 11/2013 | Yuen et al. |
| 8,597,093 | B2 | 12/2013 | Engelberg et al. |
| 8,615,377 | B1 | 12/2013 | Yuen et al. |
| 8,620,617 | B2 | 12/2013 | Yuen et al. |
| 8,670,953 | B2 | 3/2014 | Yuen et al. |
| 8,805,348 | B2 | 8/2014 | Matsuoka |

(56) References Cited

U.S. PATENT DOCUMENTS

| | | |
|---|---|---|
| 9,449,365 B2 | 9/2016 | Roberts |
| 9,449,409 B2 | 9/2016 | Roberts |
| 2001/0055242 A1 | 12/2001 | Deshmukh et al. |
| 2002/0013717 A1 | 1/2002 | Ando et al. |
| 2002/0077219 A1 | 6/2002 | Cohen et al. |
| 2002/0082144 A1 | 6/2002 | Pfeffer |
| 2002/0109600 A1 | 8/2002 | Mault et al. |
| 2002/0178060 A1 | 11/2002 | Sheehan |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0131059 A1 | 7/2003 | Brown et al. |
| 2004/0054497 A1 | 3/2004 | Kurtz |
| 2004/0061324 A1 | 4/2004 | Howard |
| 2004/0117963 A1 | 6/2004 | Schneider |
| 2004/0152957 A1 | 8/2004 | Stivoric et al. |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102072 A1 | 5/2005 | Deakin |
| 2005/0102172 A1 | 5/2005 | Sirmans, Jr. |
| 2005/0107723 A1 | 5/2005 | Wehman et al. |
| 2005/0202934 A1 | 9/2005 | Olrik et al. |
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0020177 A1 | 1/2006 | Sea et al. |
| 2006/0025282 A1 | 2/2006 | Redmann |
| 2006/0047208 A1 | 3/2006 | Yoon |
| 2006/0047447 A1 | 3/2006 | Brady et al. |
| 2006/0089542 A1 | 4/2006 | Sands |
| 2006/0129436 A1 | 6/2006 | Short |
| 2006/0143645 A1 | 6/2006 | Vock et al. |
| 2006/0264730 A1 | 11/2006 | Stivoric et al. |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2007/0050715 A1 | 3/2007 | Behar |
| 2007/0051369 A1 | 3/2007 | Choi et al. |
| 2007/0123391 A1 | 5/2007 | Shin et al. |
| 2007/0136093 A1 | 6/2007 | Rankin et al. |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0194066 A1 | 8/2007 | Ishihara et al. |
| 2007/0208544 A1 | 9/2007 | Kulach et al. |
| 2007/0276271 A1 | 11/2007 | Chan |
| 2008/0062719 A1 | 3/2008 | Shiau et al. |
| 2008/0093838 A1 | 4/2008 | Trapper et al. |
| 2008/0125288 A1 | 5/2008 | Case |
| 2008/0140163 A1 | 6/2008 | Keacher et al. |
| 2008/0140338 A1 | 6/2008 | No et al. |
| 2008/0249836 A1 | 10/2008 | Angell et al. |
| 2009/0018797 A1 | 1/2009 | Kasama et al. |
| 2009/0043531 A1 | 2/2009 | Kahn et al. |
| 2009/0048044 A1 | 2/2009 | Oleson et al. |
| 2009/0054737 A1 | 2/2009 | Magar et al. |
| 2009/0063293 A1 | 3/2009 | Mirrashidi et al. |
| 2009/0171788 A1 | 7/2009 | Trapper et al. |
| 2009/0271147 A1 | 10/2009 | Sugai |
| 2010/0331145 A1 | 12/2010 | Lakovic et al. |
| 2010/0331657 A1 | 12/2010 | Mensinger et al. |
| 2011/0003665 A1 | 1/2011 | Burton et al. |
| 2011/0009051 A1 | 1/2011 | Khedouri et al. |
| 2011/0009727 A1 | 1/2011 | Mensinger et al. |
| 2011/0022349 A1 | 1/2011 | Stirling et al. |
| 2011/0032105 A1 | 2/2011 | Hoffman et al. |
| 2011/0080349 A1 | 4/2011 | Holbein et al. |
| 2011/0106449 A1 | 5/2011 | Chowdhary et al. |
| 2011/0126143 A1 | 5/2011 | Williams et al. |
| 2011/0131005 A1 | 6/2011 | Ueshima et al. |
| 2011/0193704 A1 | 8/2011 | Harper et al. |
| 2012/0020649 A1 | 1/2012 | Vanderkaden |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0183939 A1 | 7/2012 | Aragones et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0265326 A1 | 10/2012 | Prstojevich et al. |
| 2012/0265480 A1 | 10/2012 | Oshima |
| 2012/0274508 A1* | 11/2012 | Brown .................. G04F 10/00 342/357.25 |
| 2012/0316471 A1 | 12/2012 | Rahman et al. |
| 2012/0330109 A1 | 12/2012 | Tran |
| 2013/0006718 A1 | 1/2013 | Nielsen et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0095459 A1 | 4/2013 | Tran |
| 2013/0096843 A1 | 4/2013 | Yuen et al. |
| 2013/0106684 A1 | 5/2013 | Weast et al. |
| 2013/0151196 A1 | 6/2013 | Yuen et al. |
| 2013/0158369 A1 | 6/2013 | Yuen et al. |
| 2013/0163390 A1 | 6/2013 | Gossweiler, III et al. |
| 2013/0231574 A1 | 9/2013 | Tran |
| 2013/0267249 A1 | 10/2013 | Rosenberg |
| 2013/0268236 A1 | 10/2013 | Yuen et al. |
| 2013/0280682 A1 | 10/2013 | Levine et al. |
| 2013/0310896 A1 | 11/2013 | Mass |
| 2013/0325396 A1 | 12/2013 | Yuen et al. |
| 2013/0325399 A1 | 12/2013 | Yuen et al. |
| 2014/0035761 A1 | 2/2014 | Burton et al. |
| 2014/0039804 A1 | 2/2014 | Park et al. |
| 2014/0039839 A1 | 2/2014 | Yuen et al. |
| 2014/0039840 A1 | 2/2014 | Yuen et al. |
| 2014/0039841 A1 | 2/2014 | Yuen et al. |
| 2014/0039842 A1 | 2/2014 | Yuen et al. |
| 2014/0052790 A1 | 2/2014 | Yuen et al. |
| 2014/0067278 A1 | 3/2014 | Yuen et al. |
| 2014/0107493 A1 | 4/2014 | Yuen et al. |
| 2014/0125491 A1 | 5/2014 | Park et al. |
| 2014/0127996 A1 | 5/2014 | Park et al. |
| 2014/0129243 A1 | 5/2014 | Utter, II |
| 2014/0135631 A1 | 5/2014 | Brumback et al. |
| 2014/0142403 A1 | 5/2014 | Brumback et al. |
| 2014/0143064 A1 | 5/2014 | Tran |
| 2014/0143737 A1 | 5/2014 | Mistry et al. |
| 2017/0004639 A1 | 1/2017 | Roberts |

OTHER PUBLICATIONS

"Quick Installation Guide", Withings Pulse, Jul. 24, 2013, 16pgs. withings.com/pulse.

Cooper, Daniel, "Withings Pulse review", Aug. 16, 2013, http://www.engadgel.com/2013/08/16/withings-pulse- review/, (pp. 1-8, total 8 pages).

Desmarais, Christina, "Which New Activity Tracker is Best for You?", Sep. 3, 2013, retrieved Sep. 23, 2013, retrieved from http:l/www.techlicious.com/guide/which-new-activity-tracker-is-right-for-you/, (pp. 1-4, total 4 pages).

Lester, Jonathan et al., "Validated Caloric Expenditure Estimation using a Single Body-Worn Sensor", UbiComp 2009, Sep. 30-Oct. 3, 2009, Orlando, Florida, USA, ACM 978-1-60558-431-7/09/09 (pp. 225-234, total 10 pages).

Intersema, "Using MS5534 for altimeters and barometers", AN501. doc, Application Note, www.intersema.ch, (pp. 1-12, total 12 pages).

Suunto Lumi "User Guide" Jun. 2007, Sep. 2007, 49 pages.

VTI Technologies Oy, "SCP100-D01/D11 Pressure Sensor as Barometer and Altimeter", Application Note 33, www.vti. fi, 3 pgs.

"Forerunner 405 Owner's Manual: GPS-Enabled Sports Watch With Wireless Sync", Mar. 2011, Garmin Ltd. or its subsidiaries, Part No. 190-00700-00 Rev. D, 54 pgs.

(56) References Cited

OTHER PUBLICATIONS

"Forerunner 410 Owner's Manual: GPS-Enabled Sports Watch With Wireless Sync", Jul. 2012, Garmin Ltd. or its subsidiaries, Part No. 190-01274-00 Rev. B, 50 pgs.

"Forerunner 405CX Owner's Manual: GPS-Enabled Sports Watch With Wireless Sync", Mar. 2009, Garmin Ltd. or its subsidiaries, Part No. 190-01066-00 Rev. B, 55 pgs.

"Forerunner 310XT Owner's Manual: Multisport GPS Training Device", 2009, Garmin Ltd. or its subsidiaries, Part No. 190-01066-00 Rev. B, 56pgs.

Ohtaki, Yasuaki et al., "Automatic classification of ambulatory movements and evaluation of energy consumptions utilizing accelerometers and a barometer", Microsyst Technol (2005) 11, DOI: 10.1007/s00542-005-0502-z, (pp. 1034-1040, total 7 pages).

Retscher, G. "An Intelligent Multi-sensor System for Pedestrian Navigation", Journal of Global Positioning Systems, (2006), vol. 5, No. 1-2, (pp. 110-118, 9 total pages).

Clifford, Michelle et al., "Altimeter and Barometer System", Freescale Semiconductor Application Note, AN1979, Rev. 3, Nov. 2006, 10 pgs.

Parkka, Juha et al., "Activity Classification Using Realistic Data From Wearable Sensors", IEEE Transactions on Information Technology in Biomedicine, vol. 10, No. 1, Jan. 2006, (pp. 119-128, total 10 pages).

DC Rainmaker, "Basis Bi Watch In-Depth Review", Feb. 4, 2014, http://www.dcrainmaker.com/2013/07/basis-bi-review.html, 56 pgs.

Lester, Jonathan et al., "A Hybrid Discriminative/Generative Approach for Modeling Human Activities", IJCAI'05 Proceedings of the 19th International Joint Conference on Artificial Intelligence, 2005, 7pgs.

"Activator is One of the Best Cydia iPhone Hacks", retrieved on Jul. 9, 2013, download from http://www.iphone-tips-and-advice.com/activator.html, 10 pgs.

"Forerunner 50 Owner's Manual: With ANT+Sport wireless technology", Nov. 2007, Garmin Ltd. or its subsidiaries, Part No. 190-00839-00 Rev. E, 44 pgs.

"Forerunner 10 Owner's Manual", Aug. 2012, Garmin Ltd. or its subsidiaries, Part No. 190-01472-00_0A, 8 pgs.

"Forerunner 110 Owner's Manual: GPS-Enabled Sports Watch", Dec. 2010, Garmin Ltd. or its subsidiaries, Part No. 190-01154-00 Rev. D, 16 pgs.

"Forerunner 201 Personal Trainer Owner's Manual", Feb. 2006, Garmin Ltd. or its subsidiaries, Part No. 190-00318-00 Rev. F, 48 pgs.

"Forerunner 210 Owner's Manual: GPS-Enabled Sports Watch", Dec. 2010, Garmin Ltd. or its subsidiaries, Part No. 190-01273-00 Rev. B, 28 pgs.

U.S. Office Action dated Sep. 18, 2014, in U.S. Appl. No. 14/250,635.

U.S. Final Office Action dated Dec. 24, 2014, in U.S. Appl. No. 14/250,635.

U.S. Notice of Allowance dated Mar. 23, 2016, in U.S. Appl. No. 14/250,635.

U.S. Office Action dated Sep. 16, 2014, in U.S. Appl. No. 14/250,590.

U.S. Final Office Action dated Feb. 11, 2015, in U.S. Appl. No. 14/250,590.

U.S. Office Action dated Oct. 27, 2015, in U.S. Appl. No. 14/250,590.

U.S. Notice of Allowance dated May 26, 2016, in U.S. Appl. No. 14/250,590.

U.S. Office Action dated Dec. 6, 2017, in U.S. Appl. No. 15/266,223.

\* cited by examiner

PERSONALIZED SCALING OF GRAPHICAL INDICATORS

CROSS REFERENCE TO RELATED APPLICATION

This is a continuation of co-pending prior U.S. patent application Ser. No. 14/250,635, filed on Apr. 11, 2014, entitled "PERSONALIZED SCALING OF GRAPHICAL INDICATORS", which is incorporated herein by reference in its entirety for all purposes.

BACKGROUND

Field

The embodiments described below relate to the generation and presentation of activity-related graphics. Some embodiments relate to the generation and presentation of graphical indicators conforming to a personalized display scale.

Description

The benefits of monitoring fitness-related information are well-known. A conventional stationary exercise device may include a display which graphically presents information such as time elapsed, heart rate, calories burned, etc. Wearable/portable fitness monitors also display fitness-related information to users. This information provides motivation, immediate feedback, and a better understanding of progress toward fitness goals.

Fitness-related information is typically presented using alphanumeric characters (e.g., "110 BPM") or graphical visualizations. For example, a bar chart may present a heart rate over time. Such a bar chart may include several bars, each associated with a different time interval, where the length of a bar represents a heart rate during its associated time interval.

Graphical visualizations may provide an intuitive understanding of underlying fitness-related information. However, improvements to such graphical visualizations are desired, which may result in improved understanding of the underlying information, utilization of display screen area, and/or other benefits.

SUMMARY

Some embodiments relate to a device, method, and/or computer-readable medium storing processor-executable process steps to receive from a user, via a sensor, first data indicative of activity of the user, determine one or more values of a metric based on the first data, determine a display scale based on the one or more values, receive from the user, via the sensor, second data indicative of activity of the user over a time interval, determine a second value of the metric based on the second data, generate a graphical indicator representing the second value based on the display scale and the second value, and display the graphical indicator on a display.

Some aspects further include reception from the user, via the sensor, third data indicative of activity of the user over a second time interval, determination of a third value of the metric based on the third data, generation of a second graphical indicator representing the third value based on the display scale and the third value, and display of the second graphical indicator on the display.

In some aspects, the value of the metric associated with a respective time interval is indicative of physical activity during the respective time interval. For example, the metric may be step count, heart rate, distance traveled, activity level, altitude ascended, altitude descended, floors climbed, or calories burned.

According to some aspects, the display scale indicates a length per N units of the metric. The display scale may also or alternatively indicate a number of icons per N units of the metric.

In some aspects, a position of the displayed graphical indicator on the display indicates the time interval. The position may be along an arc of a circle, wherein arcs of the circle represent a plurality of time intervals.

According to some aspects, first data indicative of activity of a user is received, one or more values of a metric are determined based on the first data, a display scale is determined based on the one or more values, second data indicative of activity of the user over a time interval is received, a second value of the metric is determined based on the second data, a graphical indicator representing the second value is generated based on the display scale and the second value, and data representing the graphical indicator is transmitted to a display device.

Further aspects include reception of third data indicative of activity of the user over a second time interval, determination of a third value of the metric based on the third data, generation of a second graphical indicator representing the third value based on the display scale and the third value, and transmission of the second graphical indicator to the display device.

According to some aspects, the display scale indicates a length per N units of the metric. The display scale may also or alternatively indicate a number of icons per N units of the metric.

A more complete understanding of some embodiments can be obtained by referring to the following detailed description and to the drawings appended hereto.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

Figure 1:
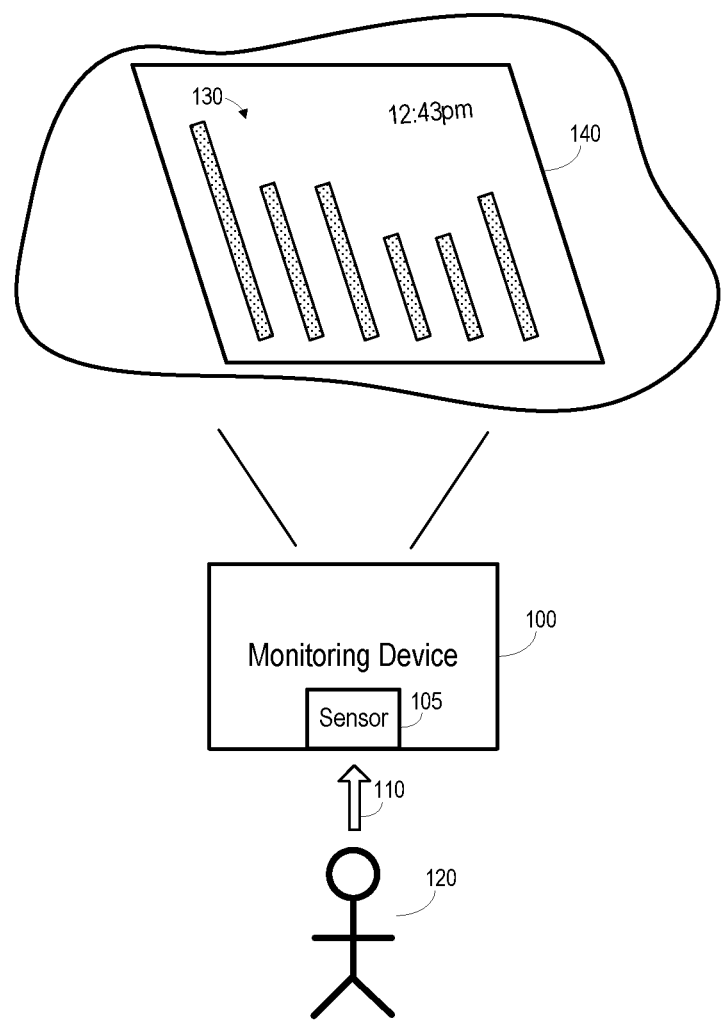
FIG. 1 illustrates operation according to some embodiments.

The following description is provided to enable any person in the art to make and use the described embodiments. Various modifications, however, will remain readily apparent to those in the art.

A brief example will now be described with reference to FIG. 1 in order to provide an introduction to various features. Embodiments are not limited to the features or description of this example.

Monitoring device 100 receives data 110 from user 120. Data 110 is received via sensor 105, and is indicative of activity of user 120. Data 110 may be received over any suitable time interval. According to some embodiments, sensor 105 is a heart rate sensor and data 110 comprises signals detected from user 120 by sensor 105.

One or more values of a metric are determined based on data 110. Continuing the example, sensor 105, alone or in conjunction with other elements of monitoring device 100 determines a heart rate of user 120 based on data 110. According to some embodiments, the determined heart rate may comprise an average heart rate during the time interval over which data 110 was received, a maximum heart rate over the time interval, an average heart rate over each of several sub-intervals of the time interval, and/or any other measure of heart rate.

Next, a display scale is determined based on the determined value or values. The display scale associates units (e.g., BPM) of the metric (e.g., heart rate) with a characteristic of a graphical indicators which will be used to represent future values of the metric. In a specific example, a determined maximum heart rate is 150 BPM and a display area is 3.2 cm in height. Accordingly, the determined display scale may be 50 BPM/1 cm. A corresponding graphical indicator representing 150 BPM is 3 cm in length, and is therefore able to fit in the display area. Moreover, additional display height (i.e., 0.2 cm) is available if the heart rate exceeds 150 BPM. If the determined maximum heart rate is 180 BPM, the determined display scale may be 60 BPM/1 cm.

After the display scale is determined, second data indicative of user activity is received over a time interval. Again, the second data may be received from user 120 by sensor 105. A second value of the metric is determined based on the second data, and a graphical indicator representing the second value is generated based on the display scale and the second value.

For example, it will be assumed that a value of 125 BPM is determined based on the second data. Based on the previously-determined display scale of 50 BPM/1 cm, a graphical indicator having a length of 2.5 cm is generated.

The graphical indicator is then displayed. FIG. 1 shows graphical indicators 130 displayed on display 140. Display 140 may comprise any type of display screen that is or becomes known, and may be integral with or separate from monitoring device 100. Each of graphical indicators 130 is generated based on the display scale described above, and each of graphical indicators 130 represents a value of a metric over a respective time interval. For example, each of indicators 130 may represent an average heart rate over a particular five minute interval.

As described, the display scale used to generate indicators 130 is determined based on metric values which were determined from signals received from user 120. Accordingly, the display scale may optimize a usage of a display area of display 140 based on the user's prior activity.

Embodiments are not limited to the graphical indicators of FIG. 1. Moreover, the metric may comprise any metric that is or become known. According to some embodiments, the metric is one of step count, heart rate, distance traveled, activity level, altitude changes, altitude ascended, altitude descended, floors climbed, and calories burned. The metric may be indicative of physical activity, but embodiments are not limited thereto.

In the present disclosure, the term "activity" includes sedentary and nonsedentary activities. As such, the metric may be associated with activities related to sleeping, lying, sitting, and standing stationary (for example, time asleep, the onset, duration, and number of awakenings while attempting to sleep, the time spent in various stages of sleep, sleep latency, sleep efficiency and other sleep quality parameters, the presence of sleep apnea and other diagnostic measures, time spent in a prone non-standing state, and resting heart rate).

Figure 2:
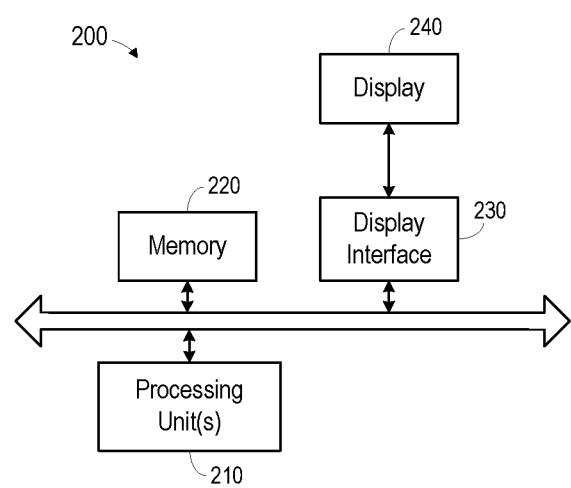
FIG. 2 is a block diagram of a device according to some embodiments.

FIG. 2 is a block diagram of system 200 according to some embodiments. System 200 may be operated to generate and display graphical indicators according to some embodiments. System 200 includes one or more processing units 210 (e.g., processor cores and/or processing threads, discrete or integrated logic, and/or one or more state machines, and/or field programmable gate arrays (or combinations thereof)). One or more processing units 210 are configured to execute processor-executable program code to cause system 200 to operate as described herein, and memory 220 for storing the program code and any other suitable data, including but not limited to values of metrics associated with respective time intervals, and user-specific display scales associated with various metrics. Memory 220 may comprise one or more fixed disks, solid-state random access memory, and/or removable media (e.g., a thumb drive) mounted in a corresponding interface (e.g., a USB port).

Display interface 230 provides communication with display 240, which may comprise any system for visual presentation of information that is or becomes known. Display 240 may comprise a touch screen for receiving user input into system 200 according to some embodiments.

One or more processing units 210 may therefore execute processor-executable program code stored in memory 220 to cause system 200 to receive first data indicative of activity of a user, to determine one or more values of a metric based on the first data, to determine a display scale based on the one or more values, to receive second data indicative of activity of the user over a time interval, to determine a second value of the metric based on the second data, to generate a graphical indicator representing the second value based on the display scale and the second value, and to display the graphical indicator on display 240.

According to some embodiments, system 200 comprises an integrated device such as, but not limited to, a wearable unit (e.g., around wrist, around neck) or an otherwise portable unit (e.g., a smartphone, a dedicated music player, a fob). In some embodiments, elements of system 200 may be embodied in separate devices, such as a server device (e.g., a desktop computer) including elements 210, 220 and 330, and a terminal device (e.g., a watch) including display 240. System 200 may perform functions other than those attributed thereto herein, and may include any elements which are necessary for the operation thereof Some embodiments of system 200 include a portable monitoring device having a physical size and shape adapted to couple to the body of a user, which allows the user to perform normal or typical user activities (including, for example, exercise of all kinds and type) without hindering the user from performing such activities. The portable monitoring device may include a mechanism (for example, a clip, strap and/or tie) that facilitates coupling or affixing the device to the user during such normal or typical user activities.

For example, during operation, an altitude sensor generates data which is representative of the altitude and/or changes in altitude of the user. A motion sensor generates data which is representative of motion of the user. The data which is representative of the altitude and/or changes in altitude and the data which is representative of the motion of the user, is used to determine energy and/or calorie "burn" of the user.

The data may also be used to determine other activity-related metrics including, for example, (i) in the context of running/walking on level, substantially level, or relatively level ground, (a) number of steps, which may be categorized according to the number of steps associated with a user state, for example, walking, jogging and/or running, (b) distance traveled and/or (c) pace, (ii) in the context of running/jogging/walking/jumping on stairs, hills or ground having a grade of greater than, for example, about 3%, (a) number of stair and/or hill steps, which may be categorized, correlated or organized/arranged according to the number of stair and/or hill steps pertaining to, for example, the speed, pace and/or user state of the user (for example, walking, jogging and/or running), (b) number of flights of stairs, (c) ascent/descent distance on stairs and/or hills, (d) pace, (e) ascent/descent on elevators and/or escalators, (f) number of calories burned or expended by walking/running on stairs and/or hills and/or (g) quantify/compare the additional calories expended or burnt from stairs/hills relative to, versus or over level ground, (iii) in the context of swimming, number of strokes, time between strokes, leg kicks and similar metrics (variance of stroke time, mean stroke time, etc.), depth underwater, strokes per lap, lap time, pace and/or distance, (iv) in the context of using a bicycle, wheelchair, skateboard, skis, snowboard, ladder, etc., (a) ascent/descent distance traversed, (b) number of additional calories expended, (c) time of a downward "run" or upward "climb", (d) number of calories expended, (e) number of pedal rotations, (f) arm or wheel rotation, (g) the grade of the surface, (h) pushes, kicks and/or steps. This list of activities (if applicable to the particular embodiment) is merely exemplary and is not intended to be exhaustive or limiting.

Figure 3:
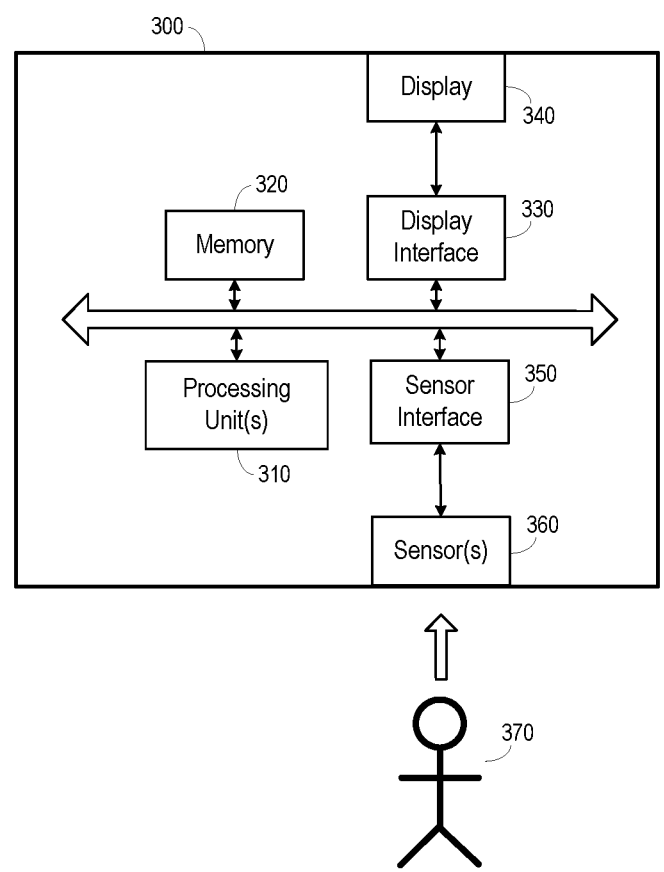
FIG. 3 is a block diagram of a device according to some embodiments.

FIG. 3 is a block diagram of device 300 according to some embodiments. Device 300 may comprise an implementation of system 200 of FIG. 2. Device 300 incorporates elements 310 through 360 into a single integrated package.

Elements 310 through 340 of device 300 may operate as described above with respect to similarly-numbered elements of system 200. Device 300 further includes sensor interface 350 for exchanging data with one or more sensors 360.

Sensors 360 may comprise any sensors for acquiring data based on which metric values may be determined. Examples of sensors 360 include, but are not limited to, an accelerometer, a light sensor, a blood oxygen sensor, a gyroscope, a magnetometer, a Global Positioning System device, a proximity sensor, an altimeter, and a heart rate sensor. One or more of sensors 360 may share common hardware and/or software components.

A value of a metric may be determined based on data acquired by one or more of sensors 360. For example, a value of a "distance traveled" metric may be determined based on the outputs of a Global Positioning System device and an altimeter. An "activity level" metric may be determined based on the outputs of a blood oxygen sensor and a heart rate sensor.

User 370 is pictured to indicate that, according to some embodiments, data received by sensors 360 is indicative of activity of user 370. For example, the one or more sensors 360 may receive data based on physical activity of user 370. Moreover, one or more of sensors 360 may receive data via direct contact with the user, for example during heart rate, skin temperature, and/or blood oxygen monitoring.

In some embodiments, calorie expenditure and activity level may be determined based on or using, partially or entirely, the ambulatory speed of user 370. The speed of the user may be calculated, determined and/or estimated as the user's step count over a time epoch multiplied by one or more step lengths of the user (which may be programmed, predetermined and/or estimated (for example, based on attributes of the user (for example, height, weight, age, leg length, and/or gender))). Representative energy expenditure rates expressed as metabolic equivalents per minute (MET/min) may then be estimated, obtained (for example, from a look-up table or database) and/or interpolated from a MET table which provides metabolic equivalents per minute for different user speeds. In some embodiments, step length may be one of two values that are indicative of a walking step length and a running step length dependent on the step frequency and/or acceleration characteristics of the user. In some embodiments, step length may be described as a linear function of step frequency: step length=A+B*step frequency, where A and B are parameters that may be associated with or calibrated to the user. Such parameters may be stored in memory in device 300.

In some embodiments, the speed value may be converted to calorie expenditure by multiplying the corresponding MET value by the user's Body Mass Ratio (BMR). BMR may be obtained through any of a number of well-known equations based on height, weight, gender, age, and/or athletic ability or through designated BMR measurement devices. For example, a user may have a running step length of 57 inches and take 180 running steps during 1 min. Using the method described above, the user's speed estimate is 9.8 miles per hour, which may be linearly interpolated to provide a BMR value of 15.8 MET from the MET table above.

Assuming the user's BMR to be 1.10 kcal/MET, the calorie burn of the user in the preceding minute is 17.4 kcal.

An intermediate MET calculation step is not required in this and similar methods. Calorie expenditure may be calculated directly based on speed and one or more physiological parameters of the user such as age, gender, height, weight, and/or athletic ability. Speed may also be filtered over time rather than accepted as a "raw" measurement for a given time epoch. All forms of speed estimation, and mechanisms to implement such techniques, whether now known and/or later developed, may be implemented in some embodiments Calorie consumption, burn and/or expenditure may be determined using data which is representative of the intensity of user motion for example, as provided or determined by one or more single axis or multi-axis accelerometers, based on a heart rate, based on altitude-related information (for example, from an altimeter disposed on the portable monitoring device), and/or based on any combination of factors described herein.

Figure 4:
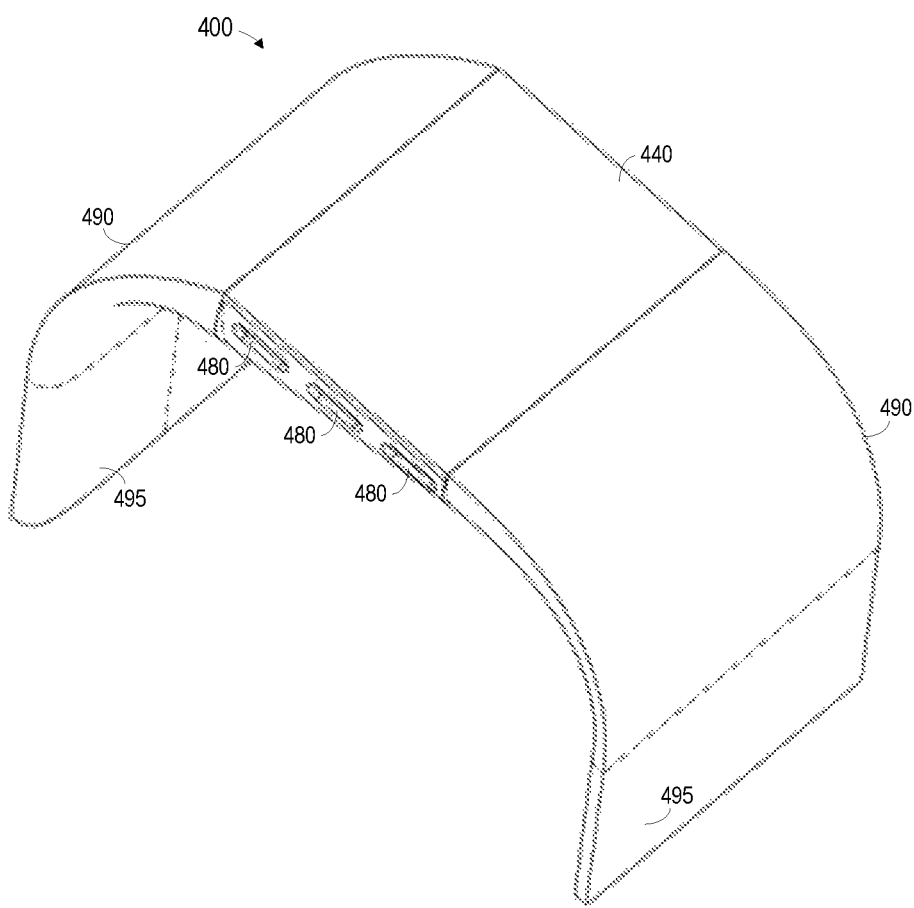
FIG. 4 is a top perspective view of a device according to some embodiments.

FIG. 4 is a top view of one implementation of device 300 according to some embodiments. According to the illustrated embodiment, device 400 is wearable on a user's wrist. Device 400 includes display 440, which may comprise any suitable type of display screen, and which may display graphical indicators as described herein. Buttons 480 may be manipulated by a user to provide input to device 400. Display 440 may also incorporate an input device (i.e., a touch screen). Band 490 may be wrapped around the wrist and is securable using securing elements 495 (e.g., hook and loop, clasp, shape memory elements).

Figure 5:
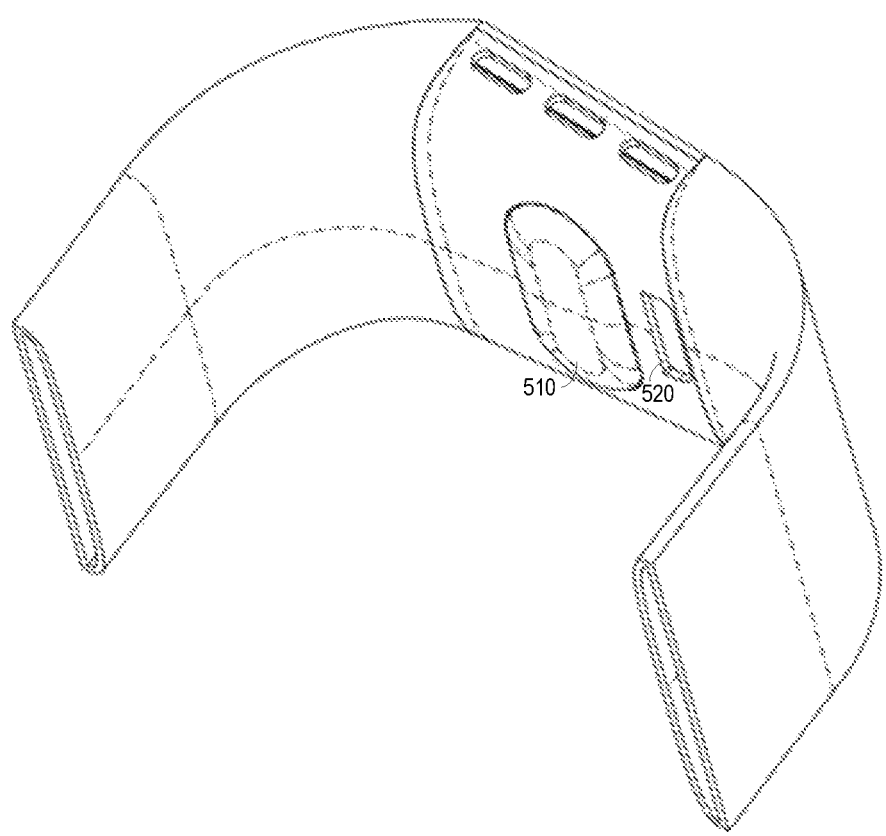
FIG. 5 is a bottom perspective view of a device according to some embodiments.

FIG. 5 is a bottom view of device 400, showing sensor protrusion 510 and power interface 520. Sensor protrusion 510 may include sensors which receive data indicative of user activity and benefit from close proximity and/or contact with a user's skin. Such sensors may include heart rate, moisture and/or temperature sensors. Power interface 520 may interface with a docking station or other power source to receive electrical charge for charging of batteries located within device 400. Embodiments are not limited to device 400 in terms of function, features and/or form factor.

Figure 6:
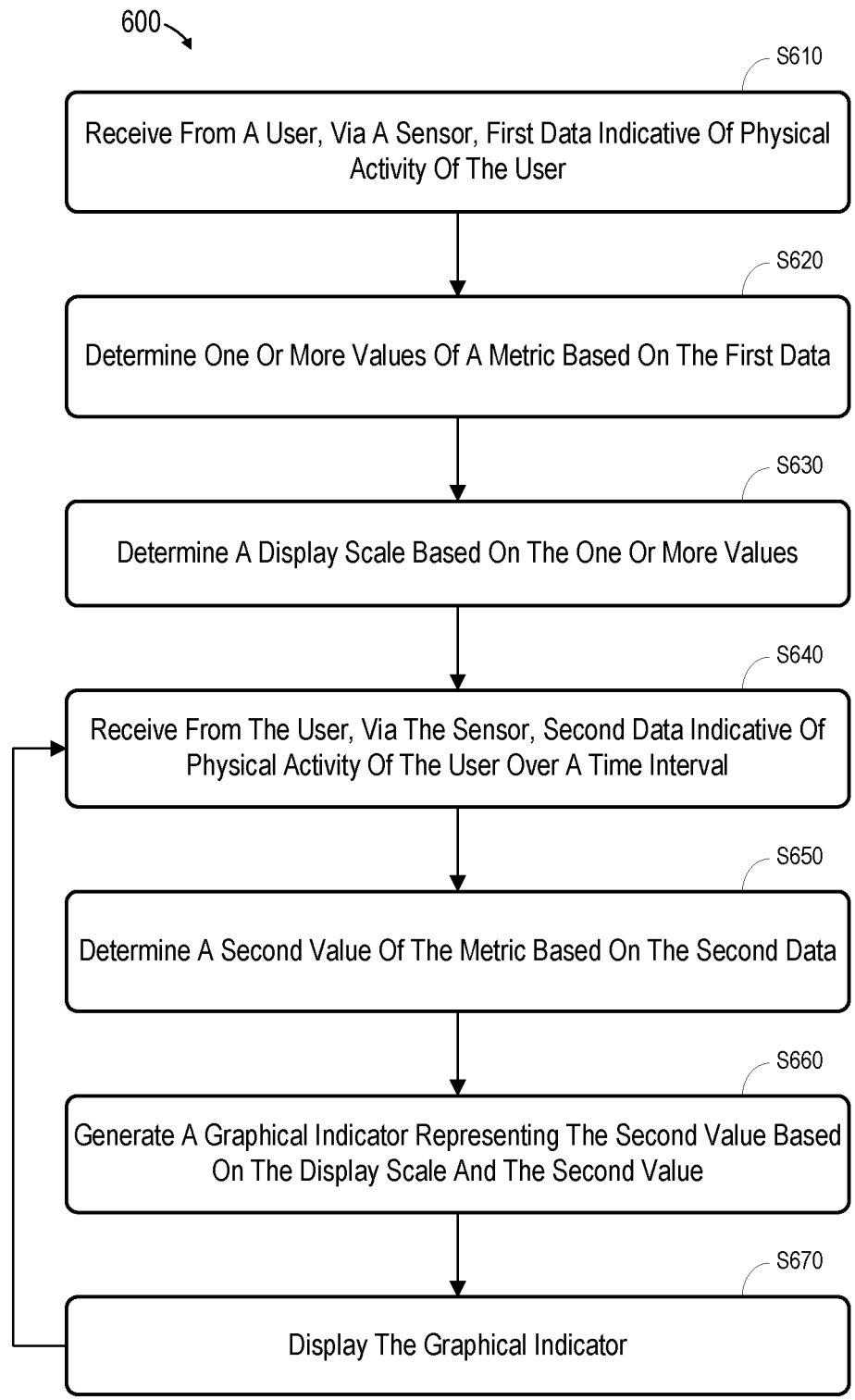
FIG. 6 is a flow diagram of a process according to some embodiments.

FIG. 6 is a flow diagram of process 600 according to some embodiments. Process 600 and the other processes described herein may be performed using any suitable combination of hardware or software, including implementations of system 200, device 300 and/or device 400. Software embodying these processes may be stored by any non-transitory tangible medium, including a fixed disk, a floppy disk, a CD, a DVD, a Flash drive, or a magnetic tape.

Initially, at S610, first data is received from a user. The first data is received via a sensor and is indicative of physical activity of the user. The first data may comprise signals acquired from any number of sensors. According to some embodiments, sensor 510 of device 400 acquires heart rate-related signals via contact with a user over a time interval. In some embodiments, an accelerometer of device 400 generates movement data due to user movement over several time intervals.

One or more values of a metric are determined at S620 based on the received data. The metric may comprise any metric described herein or that is (or becomes) known. As described with respect to FIG. 1, sensor 105, alone or in conjunction with other elements of monitoring device 100, may determine a heart rate of user 120 based on received data 110 at S620. The determined heart rate may comprise an average heart rate during the time interval over which data 110 was received, a maximum heart rate over the time interval, an average heart rate over each of several sub-intervals of the time interval, and/or any other measure of heart rate. Determination of the one or more values at S620 may also be based on stored data, such as user body characteristics, dietary information, etc.

Figure 7:
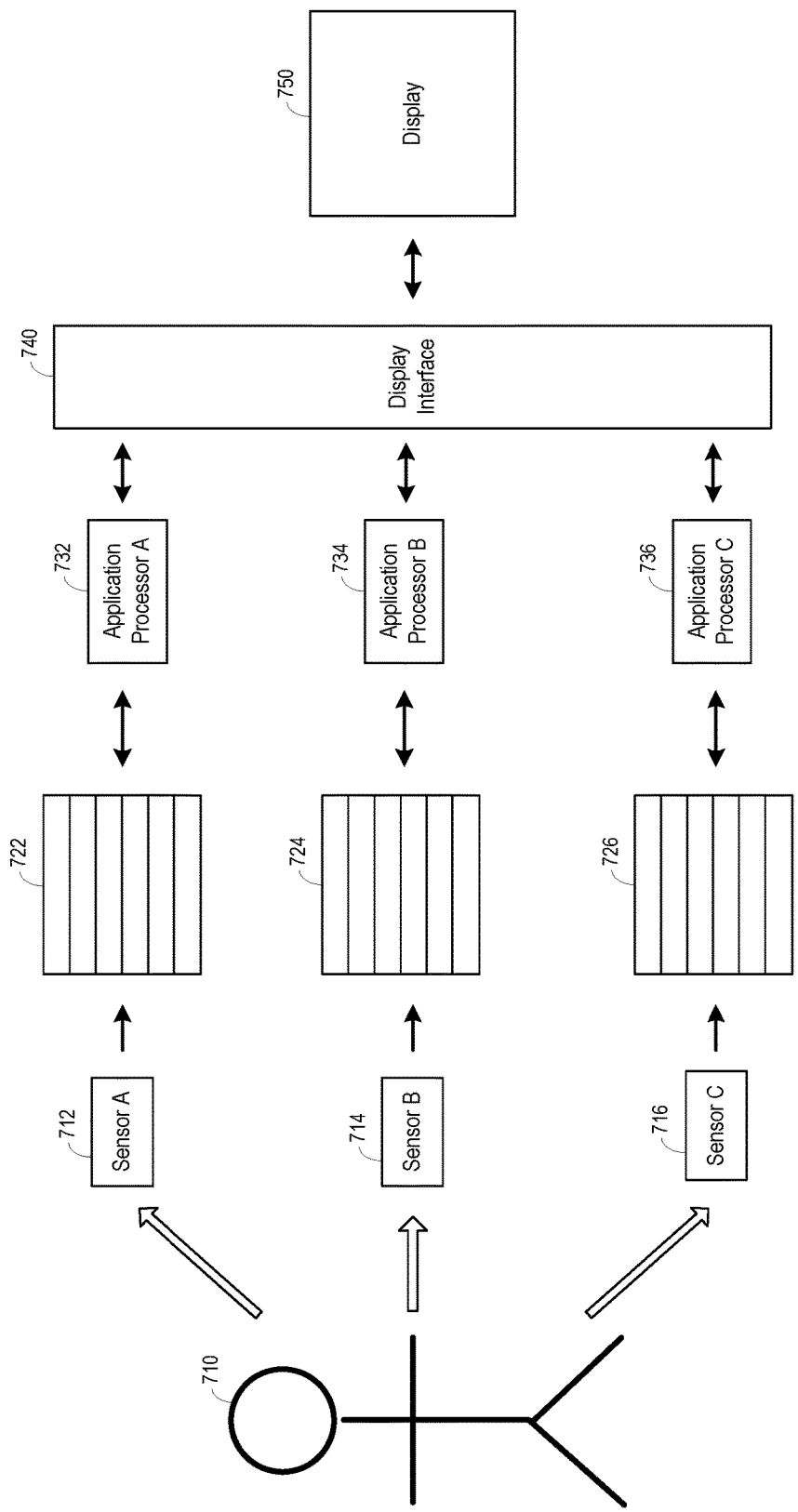
FIG. 7 illustrates operation of a system according to some embodiments.

FIG. 7 is a block diagram describing operation of system elements according to some embodiments. As shown, sensors 712, 714 and 716 receive data from user 710. Each of sensors 712, 714 and 76 may receive such data continuously or according to a respective schedule.

The received data is stored in respective ones of memory buffers 722, 724 and 726. The stored data may be raw data or data processed to any output format supported by its respective sensor. For example, according to some embodiments, sensor 714 is a heart rate sensor and outputs a current heart rate to buffer 724 at ten second intervals. Each output heart rate is stored in a memory location of buffer 724.

In some embodiments, application processors 732, 734 and 736 comprise execution threads, processor cores or other processing units for determining metric values based on the data of memory buffers 722, 724 and 726. Application processors 732, 734 and 736 may subscribe to updates of one or more of memory buffers 722, 724 and 726, and determine metric values based on data received according to the subscription. Each of application processors 732, 734 and 736 is associated with a respective metric. That is, each of application processors 732, 734 and 736 determines one or more values of a single metric and also determines a display scale associated with that metric.

In this regard, a display scale is determined at S630 based on the determined value or values. As described above, the display scale associates units of the metric with a characteristic of a graphical indicator which will be used to represent future values of the metric. Any one or more previously-determined metric values may be used to determine the display scale according to some embodiments. For example, application processor 732 may operate to determine the display scale based on metric values associated with a previous week. Values may be additionally or otherwise filtered, using any known filter, for inclusion in the determination of the display scale. Values which are several standard deviations from a mean value may be excluded, for example.

As described above, determination of the display scale may take into account a maximum display area, for example of display 750. An application processor 732, 734, and/or 736 may therefore communicate with display interface 740 at S630 to determine a size of an available display area.

According to some embodiments, a display scale may specify an area per number of units of the metric (e.g., 2 $cm^2$/5 steps). A display scale may specify a number of icons per number of units of the metric (e.g., 2 icons/50 ft. in elevation). Embodiments of a display scale may specify any graphical characteristic per number of units of the metric Next, at S640, second data indicative of user activity is received from the user over a time interval. According to some embodiments, any amount of time may pass between S630 and S640. For example, S610 through S630 may be executed during a calibration period, and flow may pause thereafter until a user operates input controls (e.g., buttons 480 and/or touch screen display 440) to enter a monitoring mode at S640.

With respect to the example of FIG. 7, the second data may be received by one or more of sensors 712, 714 and 716 and stored in respective ones of memory buffers 722, 724 and/or 726. A second value of the metric is determined at S650 based on the second data. One of application processors 732, 734 and 736 may determine the second value at S650 as described above with respect to S620.

A graphical indicator representing the second value is generated at S660 based on the display scale and the second value. One of application processors 722, 724 and 726 may generate the graphical indicators at S660. Reiterating an example described above, a display scale of 50 BPM/1 cm is determined at S630 and a value of 125 BPM is determined at S650 based on the second data. Accordingly, a graphical indicator having a length of 2.5 cm is generated at S660.

The graphical indicator is displayed at S670. Display of the graphical indicator may comprise transmitting a visualization including the graphical indicator to another device for display, or displaying the graphical indicators on an on-board display. According to some embodiments, one of application processors 722, 724 and 726 transmits the graphical indicator to display interface 740 at S670, and display interface 740 controls display 750 to display the graphical interface thereon.

FIGS. 8-11 each illustrate a displayed graphical indicator according to some embodiments of S670. FIGS. 8-11 are intended to demonstrate examples of visualizations which include graphical indicators according to some embodiments, but embodiments are not limited thereto.

Figure 8:
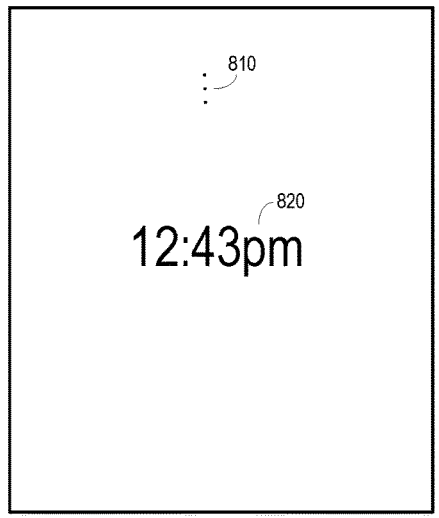
FIG. 8 is an outward view of a displayed graphical indicator and a current time according to some embodiments.

FIG. 8 shows graphical indicator 810 consisting of three icons. Also shown is current time 820. For example, each icon of graphical indicator 810 may represent 30 BPM. Therefore, indicator 810 represents 90 BPM.

A position of graphical indicator 810 indicates the time interval associated with the graphical indicator. In the present example, graphical indicator 810 is positioned at the '0' minute position of a traditional analog clock layout, therefore graphical indicator 810 is associated with the 60th minute of the prior hour. More specifically, graphical indicator 810 indicates a heart rate of 90 BPM over the 60th minute of the prior hour. Accordingly, some embodiments efficiently convey values associated with respective time intervals in an intuitive manner which can be quickly grasped by a user.

Figure 9:
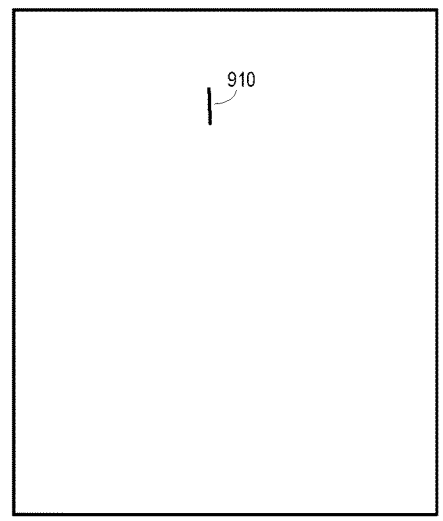
FIG. 9 is an outward view of a displayed graphical indicator according to some embodiments.

FIG. 9 shows graphical indicator 910, which is similar to graphical indicator 810 excepting that graphical indicator 910 is a solid line. The length of graphical indicator 910 represents the second value determined at S650, and is determined based on the second value and on a display scale as described above. Again, a position of graphical indicator 910 indicates the time interval associated with the graphical indicator, in this case the 60th minute of the prior hour.

Figure 10:
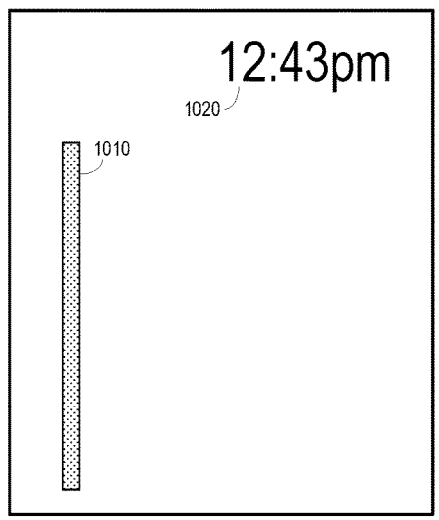
FIG. 10 is an outward view of a displayed graphical indicator and a current time according to some embodiments.

FIG. 10 shows graphical indicator 1010 and current time 1020. The length of graphical indicator 1010 is determined based on the second value determined at S650 and on a display scale as described above. The position of graphical indicator 1010 may correspond to a first ten-minute time interval since an instruction was received from the user to begin monitoring the metric.

Figure 11:
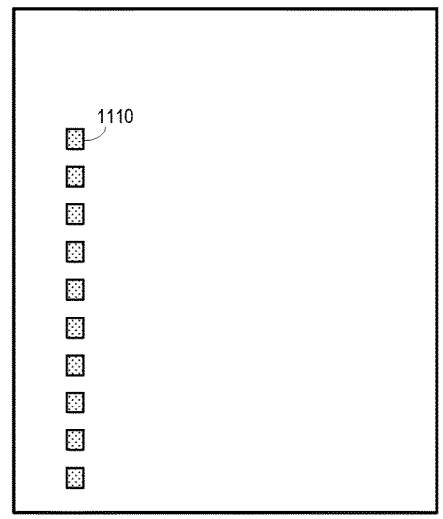
FIG. 11 is an outward view of a displayed graphical indicator according to some embodiments.

FIG. 11 shows graphical indicator 1110, which is similar to graphical indicator 1010 but is composed of icons. The number of icons of graphical indicator 1010 represents the second value determined at S650, and is determined based on the second value and on a display scale (e.g., 1 icon/10 steps). The position of graphical indicator 1110 may correspond to a first one-minute time interval since an instruction was received from the user to begin monitoring the metric.

Returning to process 600, flow continues from S670 to S640 to receive additional data from the user. Accordingly, flow cycles between S640 and S670 to receive new data indicative of physical activity, to determine new matric values based on the data, and to generate and display new graphical indicators based on the values and on the previously-determined display scale.

The new graphical indicators may be displayed along with previously-generated and displayed indicators so as to convey changes in metric values over time. FIG. 12-15 illustrate the visualizations of FIGS. 8-11 after several iterations of S640-S670 according to some embodiments.

Figure 12:
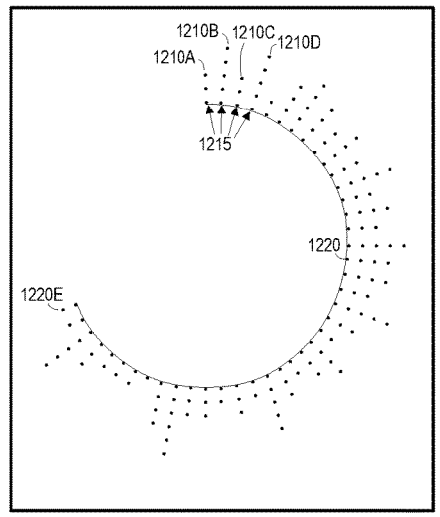
FIG. 12 is an outward view of displayed graphical indicators and a current time according to some embodiments.

FIG. 12 shows a plurality of graphical indicators, each of which represents a value of a metric and a time interval. As described above, the time interval associated with a graphical indicator is indicated by a position of the graphical indicator. The ends of each graphical indicator substantially trace an arc of circle 1220, and the position of an end of a graphical indicator on arc 1220 indicates the time interval associated with the graphical indicator.

More specifically, distal ends 1215 of graphical indicators 1210A through 1210D are located on arc 1220 at the :00, :01, :02 and :03 positions of an analog clock, respectively. These positions correspond to time intervals which are one minute in length. The time intervals associated with each graphical indicator may exhibit any duration. For example, each position of an end 1215 may correspond to a five minute interval, a ten minute interval, or an interval of any duration. In a case that a complete circle includes sixty graphical indicators and corresponds to twelve hours, each graphical indicator is associated with a twelve minute interval. Similarly, in a case that a complete circle includes sixty graphical indicators and corresponds to twenty-four hours, each graphical indicator is associated with a twenty-four minute interval.

Figure 13:
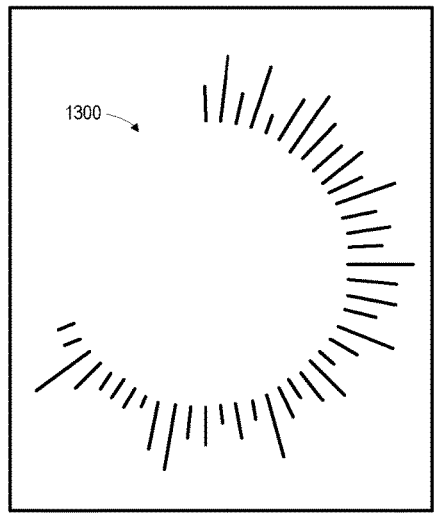
FIG. 13 is an outward view of displayed graphical indicators according to some embodiments.

FIG. 13 is an outward view of visualization 1300 according to some embodiments. Visualization 1300 is identical to FIG. 12 except that each graphical indicator is a solid. The ends of each of the graphical indicators of visualization 1300 substantially trace an arc of a circle, and a position of an end of a graphical indicator on the arc of the circle indicates the time interval associated with the graphical indicator.

Figure 14:
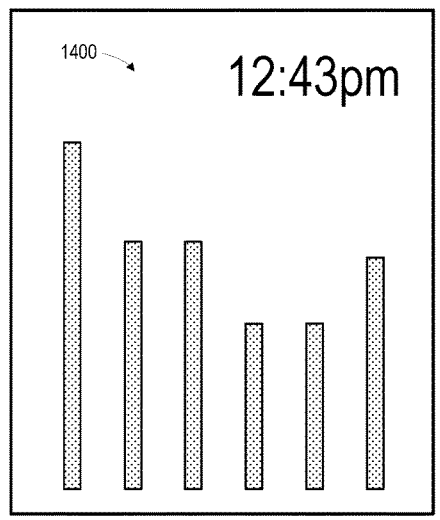
FIG. 14 is an outward view of displayed graphical indicators and a current time according to some embodiments.

FIG. 14 shows graphical indicators displayed in addition to graphical indicator 1010 of FIG. 10. Each of the graphical indicators of visualization 1400 may be generated based on a same display scale at S660. According to the illustrated embodiment, the display scale associates a length of a graphical indicator with a number of units of a metric.

Figure 15:
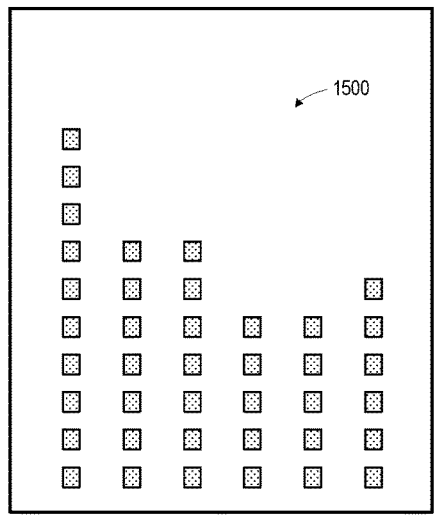
FIG. 15 is an outward view of displayed graphical indicators according to some embodiments.

Visualization 1500 of FIG. 15 shows graphical indicators displayed in addition to graphical indicator 1110 of FIG. 11. The graphical indicators of visualization 1500 may be generated based on a same display scale, which associates a number of icons of a graphical indicator with a number of units of a metric.

Embodiments are not limited to the graphical indicators described herein. A visualization according to some embodiments may include two or more types of graphical indicators. A visualization according to some embodiments may also include displayed elements in addition to the graphical indicators and other elements shown herein.

According to some embodiments, flow may occasionally return to S630 to determine a new display scale. For example, the display scale may be determined based on data which was received after the original determination of the display scale. This re-determination may occur daily, weekly, monthly, or in response to any condition, such as a determination that the determined metric values consistently meet (or fail to meet) a threshold. Such a feature may account for changes in the user's fitness and/or physiology.

Process 600 may pause or terminate at any time according to some embodiments. For example, a user may input an instruction to switch a monitoring mode, causing termination of process 600. Data may continue to be received from the user as described herein despite termination of process 600, and that data may be used to determine a display scale upon resumption of process 600.

Figure 16A:
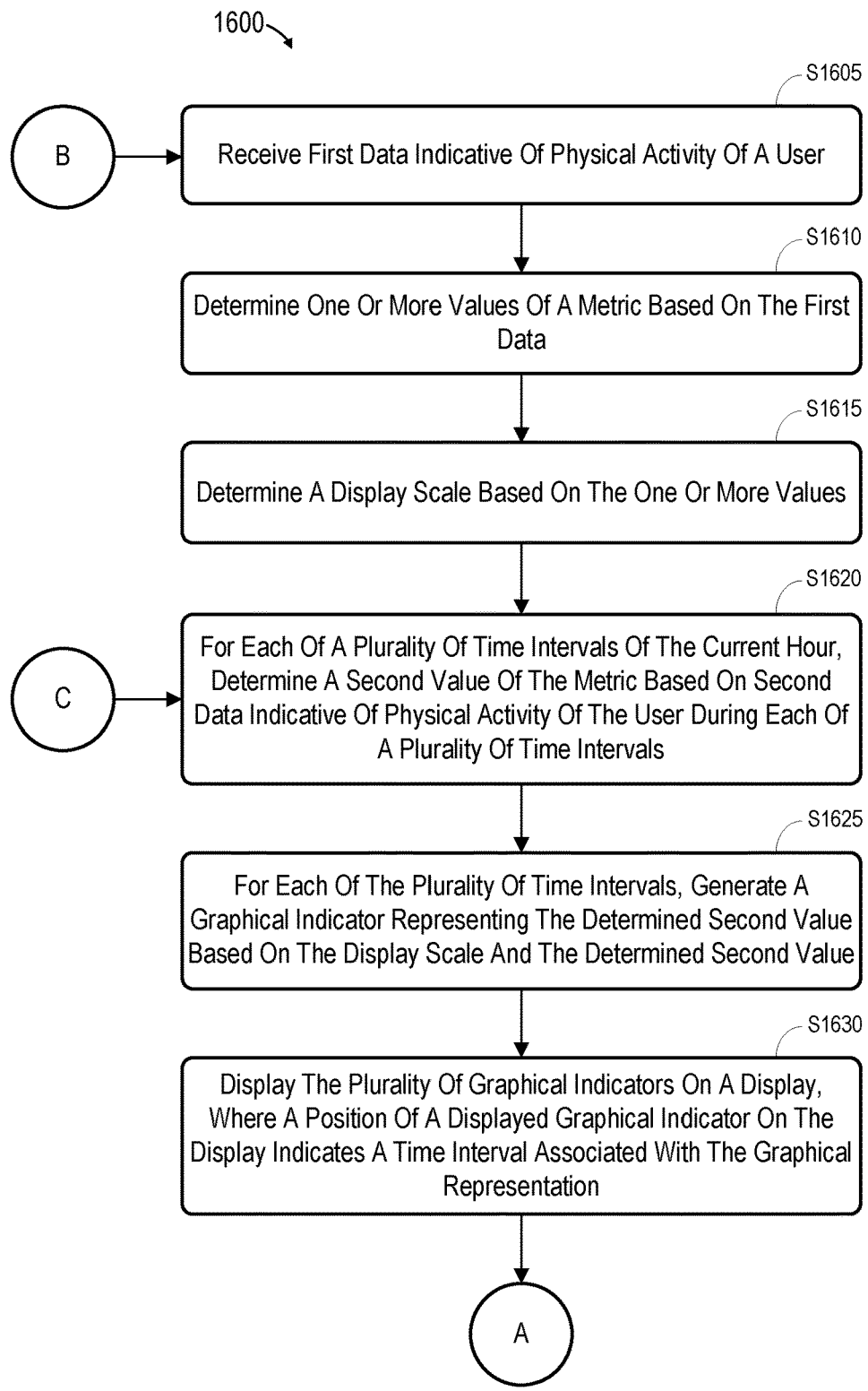
FIGS. 16A and 16B comprise a flow diagram of a process according to some embodiments.
Figure 16B:
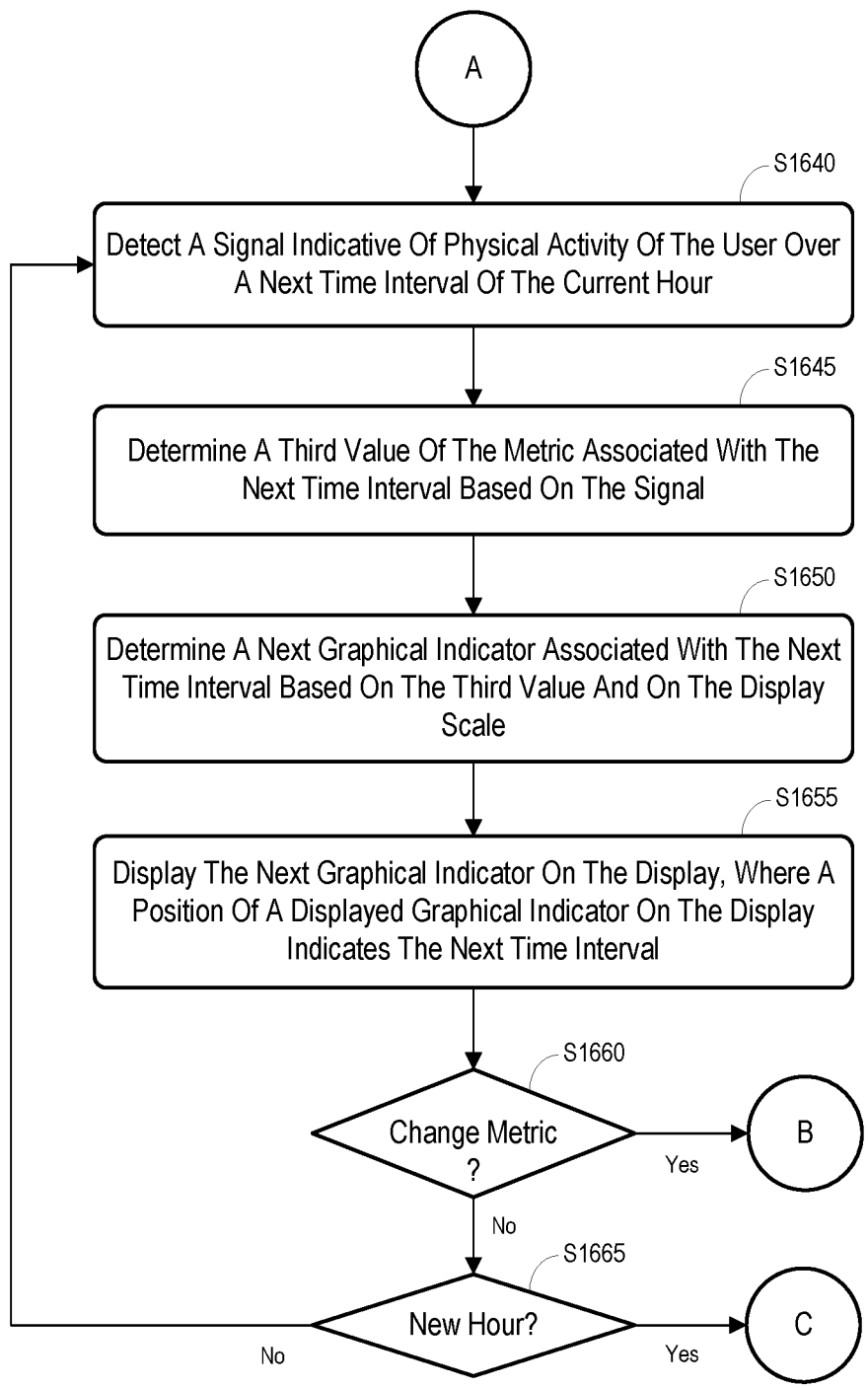

FIGS. 16A and 16B comprise process 1600 according to some embodiments. Embodiments are not, however, limited to the features of process 1600.

Prior to process 1600, it will be assumed that a device embodying process 1600 is activated (i.e., powered on, woken from sleep, etc.) or otherwise instructed to enter a mode for displaying a visualization according to some embodiments.

S1605 through S1615 may be executed as described above with respect to S610 through S630 of process 600, but implementations are not limited thereto. After execution of S630, a display scale has been determined which associates units of a metric with a characteristic of a graphical indicator which will be used to represent future values of the metric. In the present example, the metric is step count and the display scale associates a length of a graphical indicator with a number of steps.

Next, at S1620, a value of the metric is determined for each of a plurality of time intervals of the current hour. The value for each time interval is determined based on second data indicative of physical activity of the user over that time interval. The current time may be determined from a network to which the device is connected (i.e., wired or wirelessly), from an on-board clock, or by other means. For example, if a current time of 12:43 pm is determined, so a value of the metric is determined for each completed minute of the current hour (i.e., for each of forty-two completed minutes). Time intervals are not limited to single minutes in some implementations, as described above. It will be assumed that the metric in the current example is step count, therefore forty step count values are determined at S1620.

For each of the plurality of time intervals, a graphical indicator associated with the time interval is generated at S1625. The length of a graphical indicator is determined based on the display scale and on the value of the metric for the time interval associated with the graphical indicator.

Figure 17:
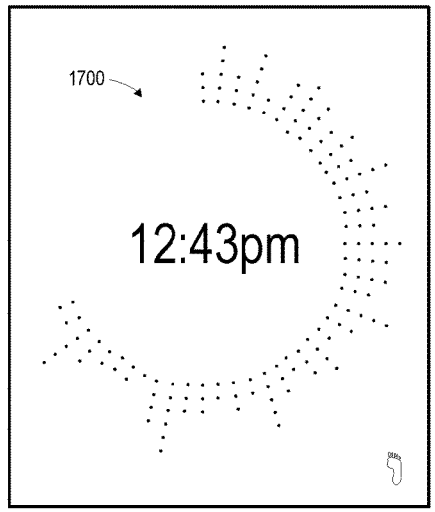
FIG. 17 is an outward view of displayed graphical indicators and a current time according to some embodiments.

The plurality of graphical indicators are displayed at S1630. According to some embodiments, a position of each of the displayed plurality of graphical indicators indicates a time interval associated with each graphical indicator. FIG. 17 provides an illustration of such a display according to the present example. The ends of each of the displayed plurality of graphical indicators substantially trace an arc of a circle, and a position of an end of a graphical indicator on the arc indicates a time interval associated with the graphical indicator.

Next, at S1640, a signal indicative of physical activity over a next time interval is detected. In the present example, the next time interval is the forty-third minute of the hour, since values have been determined for the initial forty-two minutes of the hour. The signal may be detected by a sensor such as those already described. More than one signal from more than one sensor may be detected at S1640, depending on the information needed to determine a value of the particular metric being evaluated. In this regard, a next value of the metric is determined at S1645 and, as described with respect to S650 and S660, a graphical indicator representing the next value and associated with the next time interval is determined at S1650. The length of the graphical indicator is determined based on the display scale and on the next value of the metric.

Figure 18:
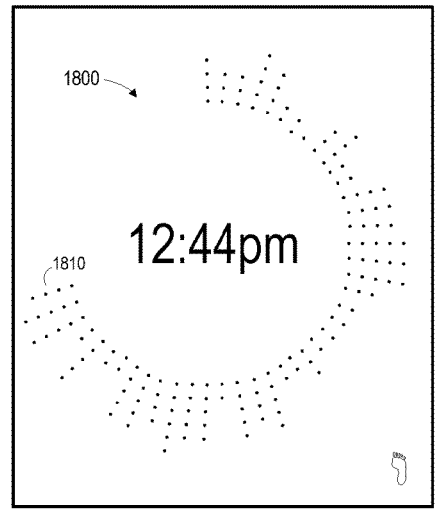
FIG. 18 is an outward view of displayed graphical indicators and a current time according to some embodiments.

As illustrated by graphical indicator 1810 of FIG. 18, the graphical indicator determined at S1650 is displayed at S1655. A position of a first end of graphical indicator 1810 on the arc indicates its associated time interval (i.e., the forty-third minute).

At S1660, it is then determined whether the metric of interest has changed. According to some embodiments, the metric of interest may change to another metric based on a schedule, in which case S1660 consists of confirming the schedule. In some embodiments, a user may issue a command to change the schedule. The command may be issued via buttons such as buttons 480, or by performing a touch screen gesture, such as a swipe, upon display 440. Any suitable input modality may be used to issue such a command.

If it is not determined to change the metric at S1660, it is determined whether the current time has entered a new hour. If not, flow continues to S1640 and to determine a new value, to generate a new graphical indicator based on the value and the display scale, and to display the new graphical indicator at an appropriate position on the arc of the circle.

Figure 19:
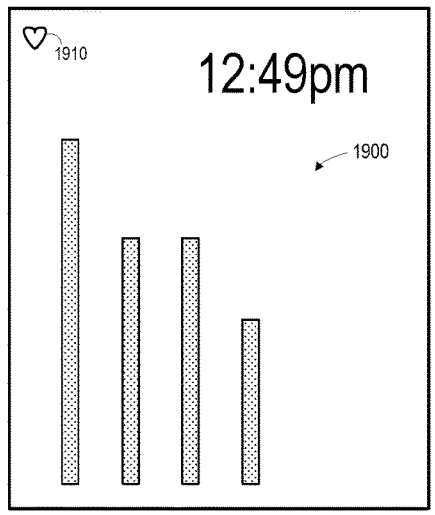
FIG. 19 is an outward view of displayed graphical indicators and a current time according to some embodiments.
Figure 20:
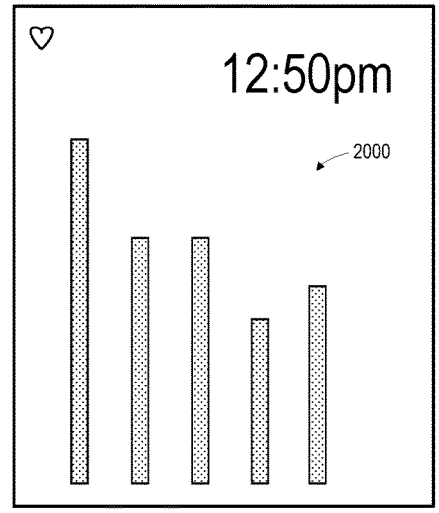
FIG. 20 is an outward view of displayed graphical indicators and a current time according to some embodiments.

Upon determining at S1660 that the metric is to be changed, flow returns to the beginning of process 1600 to determine a display scale, and to generate and display a plurality of graphical indicators based on the display scale and on values of the new metric for each time interval of the current hour. FIG. 19 illustrates display of such graphical indicators according to some embodiments. Each graphical indicator of visualization 1900 represents a value of the new metric (e.g., heart rate) associated with a time interval indicated by a position of the graphical indicator. Icon 1910 now indicates the new metric, signaling to the user that the metric has changed.

On the other hand, if it is determined at S1665 that a new hour has arrived, flow returns to S1620 to determine a plurality of values of the new metric for a plurality of time intervals of the new hour (S1620), to generate a graphical indicator for each of the values based on the display scale (S1625), and to display the graphical indicators (S1630), where a position of a displayed graphical indicator indicates a time interval associated with the graphical representation.

Figure 21:
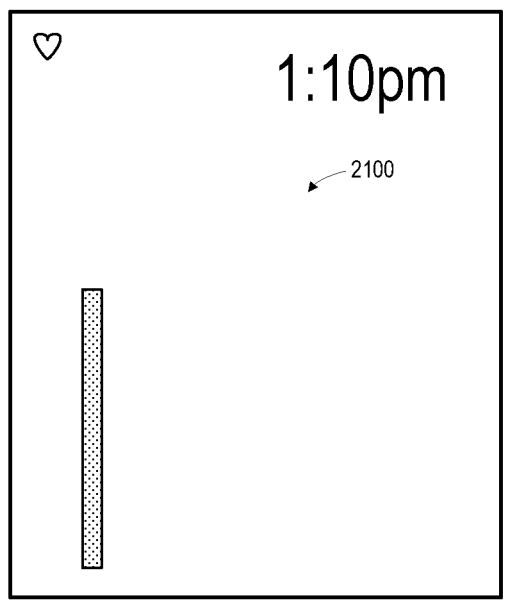
FIG. 21 is an outward view of a displayed graphical indicator and a current time according to some embodiments.

Upon returning to S1620 from S1665 during the first minute of the hour, no time intervals of the new hour will have elapsed, so the first value and graphical indicator of the current hour are determined at S1645 and S1650. The graphical indicator is displayed at S1655 as part of a new visualization, as illustrated by visualization 2100 of FIG. 21. Flow may then continue as described above to determine and display graphical indicators associated with the current metric or with another metric detected at S1660.

The foregoing diagrams represent logical architectures for describing processes according to some embodiments, and actual implementations may include more or different components arranged in other manners. Other topologies may be used in conjunction with other embodiments. Moreover, each system described herein may be implemented by any number of devices in communication via any number of other public and/or private networks. Two or more of such computing devices may be located remote from one another and may communicate with one another via any known manner of network(s) and/or a dedicated connection. Each device may include any number of hardware and/or software elements suitable to provide the functions described herein as well as any other functions. For example, any computing device used in an implementation of some embodiments may include a processor to execute program code such that the computing device operates as described herein.

All systems and processes discussed herein may be embodied in program code stored on one or more non-transitory computer-readable media. Such media may include, for example, a floppy disk, a CD-ROM, a DVD-ROM, a Flash drive, magnetic tape, and solid state Random Access Memory (RAM) or Read Only Memory (ROM) storage units. Embodiments are therefore not limited to any specific combination of hardware and software.

Those in the art will appreciate that various adaptations and modifications of the above-described embodiments can be configured without departing from the scope and spirit of the claims. Therefore, it is to be understood that the claims may be practiced other than as specifically described herein.

The invention claimed is:

1. A device, comprising:
a display;
one or more sensors;
one or more processors;
a memory; and
program code, wherein the program code is stored in the memory and configured to be executed by the one or more processors, the program code including instructions that, when executed, cause the one or more processors to:
receive, via the one or more sensors, first data indicative of activity of a user performed during a first time interval;
determine one or more first values of a metric based on the first data;
determine a first display scale based on the one or more first values of the metric, the first display scale associating N units of the metric with a first value of a graphical characteristic;
receive, via the one or more sensors, second data indicative of activity of the user performed during a second time interval having a predetermined start time and occurring after the first time interval;
determine a plurality of second values of the metric based on the second data;
determine, based on the second values of the metric and on the first display scale, corresponding second values of the graphical characteristic;
generate a first graphical indicator for each second value of the metric, each first graphical indicator exhibiting the corresponding second value of the graphical characteristic; and
display each first graphical indicator of the first graphical indicators at a corresponding position on the display, where the corresponding position of each first graphical indicator on the display indicates a time within the second time interval associated with the corresponding second value of the metric, each of the positions corresponding with one of the first graphical indicators is arranged along a first segment of a circular path, and the first segment represents the second time interval.

2. The device according to claim 1, the program code further including instructions that, when executed, cause the one or more processors to:
determine that a predetermined time period has elapsed since determination of the first display scale; and
determine, in response to the determination that the predetermined time period has elapsed, a second display scale associating M units of the metric with the first value of the graphical characteristic.

3. The device according to claim 2, the program code further including instructions that, when executed, cause the one or more processors to:

receive, via the one or more sensors, third data indicative of activity of the user performed during a third time interval occurring after the second display scale is determined;
determine a plurality of third values of the metric based on the third data;
determine, based on the third values of the metric and on the second display scale, corresponding third values of the graphical characteristic;
generate a second graphical indicator for each third value of the metric, each second graphical indicator exhibiting the corresponding third value of the graphical characteristic; and
display each second graphical indicator of the second graphical indicators at a corresponding position on the display, where the corresponding position of each second graphical indicator on the display indicates a time within the third time interval associated with the corresponding third value of the metric, each of the positions corresponding with one of the second graphical indicators is arranged along a second segment of the circular path, and the second segment represents the third time interval.

4. The device according to claim 3, wherein the positions on the display corresponding with the first graphical indicators and the second graphical indicators correspond with minute positions on a clock face.

5. The device according to claim 1, wherein the one or more sensors includes at least one sensor selected from the group consisting of:
an accelerometer;
a light sensor;
a blood oxygen sensor;
a gyroscope;
a magnetometer;
a Global Positioning System device;
a proximity sensor,
an altimeter; and
a heart rate sensor.

6. The device according to claim 1, wherein the graphical characteristic is a length and the first display scale associates a particular length of the graphical characteristic with the N units of the metric.

7. The device according to claim 1, wherein the graphical characteristic is a number of icons and the first display scale associates a particular number of icons of the graphical characteristic with the N units of the metric.

8. The device according to claim 1, wherein the metric is selected from the group consisting of: step count, heart rate, distance traveled, activity level, altitude changes, altitude ascended, altitude descended, floors climbed, and calories burned.

9. The device according to claim 1, wherein the circular path represents a sixty minute time interval.

10. The device according to claim 1, wherein a length of the first segment increments according to a measurement of current time.

11. The device according to claim 1, wherein the circular path represents a predetermined time period and a length of the first segment relative to a length of the circular path represents a proportion of the predetermined time period that has passed based on a current time.

12. A method, comprising:
receiving, via one or more sensors, first data indicative of activity of the user performed during a first time interval;

determining one or more first values of a metric based on the first data;

determining a first display scale based on the one or more first values of the metric, the first display scale associating N units of the metric with a first value of a graphical characteristic;

receiving, via the one or more sensors, second data indicative of activity of the user performed during a second time interval having a predetermined start time and occurring after the first time interval;

determining a plurality of second values of the metric based on the second data;

determining, based on the second values of the metric and on the first display scale, corresponding second values of the graphical characteristic;

generating a first graphical indicator for each second value of the metric, each first graphical indicator exhibiting the corresponding second value of the graphical characteristic; and displaying each first graphical indicator of the first graphical indicators at a corresponding position on a display, where the corresponding position of each first graphical indicator on the display indicates a time within the second time interval associated with the corresponding second value of the metric, each of the positions corresponding with one of the first graphical indicators is arranged along a first segment of a circular path, and the first segment represents the second time interval.

13. The method according to claim 12, further comprising:

determining that a predetermined time period has elapsed since determination of the first display scale; and determining, in response to the determination that the predetermined time period has elapsed, a second display scale associating M units of the metric with the first value of the graphical characteristic.

14. The method according to claim 13, further comprising:

receiving, via the one or more sensors, third data indicative of activity of the user performed during a third time interval occurring after the second display scale is determined;

determining a plurality of third values of the metric based on the third data;

determining, based on the third values of the metric and on the second display scale, corresponding third values of the graphical characteristic;

generating a second graphical indicator for each third value of the metric, each second graphical indicator exhibiting the corresponding third value of the graphical characteristic; and displaying each second graphical indicator of the second graphical indicators at a corresponding position on the display, where the corresponding position of each second graphical indicator on the display indicates a time within the third time interval associated with the corresponding third value of the metric, each of the positions corresponding with one of the second graphical indicators is arranged along a second segment of the circular path, and the second segment represents the third time interval.

15. The method according to claim 12, wherein the one or more sensors includes at least one sensor selected from the group consisting of:

an accelerometer;
a light sensor;
a blood oxygen sensor;
a gyroscope;
a magnetometer;
a Global Positioning System device;
a proximity sensor,
an altimeter; and
a heart rate sensor.

16. The method according to claim 12, wherein the metric is selected from the group consisting of: step count, heart rate, distance traveled, activity level, altitude changes, altitude ascended, altitude descended, floors climbed, and calories burned.

17. The method according to claim 12, wherein the circular path represents a twelve hour time interval.

18. The method according to claim 12, wherein a length of the first segment increments according to a measurement of current time.

19. The method according to claim 12, wherein the circular path represents a predetermined time period and a length of the first segment relative to a length of the circular path represents a proportion of the predetermined time period that has passed based on a current time.

20. The method according to claim 13, wherein the positions on the display corresponding with the first graphical indicators and the second graphical indicators correspond with minute positions on a clock face.

21. A method, comprising:

receiving first data indicative of activity of a user performed during a first time interval;

determining one or more first values of a metric based on the first data;

determining a first display scale based on the one or more first values of the metric, the first display scale associating N units of the metric with a first value of a graphical characteristic;

receiving second data indicative of activity of the user performed during a second time interval having a predetermined start time and occurring after the first time interval;

determining a plurality of second values of the metric based on the second data;

determining, based on the second values of the metric and on the first display scale, corresponding second values of the graphical characteristic;

generating a first graphical indicator for each second value of the metric, each first graphical indicator exhibiting the corresponding second value of the graphical characteristic; and transmitting data representing each first graphical indicator and information indicating a corresponding position at which to display each first graphical indicator on a display device, where the corresponding position of each first graphical indicator indicates a time within the second time interval associated with the corresponding second value of the metric, each of the positions corresponding with one of the first graphical indicators is arranged along a first segment of a circular path, and the first segment represents the second time interval.

22. The method according to claim 21, further comprising:

determining that a predetermined time period has elapsed since determination of the first display scale; and determining, in response to the determination that the predetermined time period has elapsed, a second display scale associating M units of the metric with the first value of the graphical characteristic.

23. The method according to claim 22, further comprising:

receiving third data indicative of activity of the user performed during a third time interval occurring after the second display scale is determined;

determining a plurality of third values of the metric based on the third data;

determining, based on the third values of the metric and on the second display scale, corresponding third values of the graphical characteristic;

generating a second graphical indicator for each third value of the metric, each second graphical indicator exhibiting the corresponding third value of the graphical characteristic; and transmitting data representing each second graphical indicator of the second graphical indicators and information indicating a corresponding position at which to display each second graphical indicator on the display device, where the corresponding position of each second graphical indicator indicates a time within the third time interval associated with the corresponding third value of the metric, each of the positions corresponding with one of the second graphical indicators is arranged along a second segment of the circular path, and the second segment represents the third time interval.

24. The method according to claim 23, wherein the positions on the display corresponding with the first graphical indicators and the second graphical indicators correspond with minute positions on a clock face.

25. The method according to claim 21, wherein the graphical characteristic is a length and the first display scale associates a particular length of the graphical characteristic with the N units of the metric.

26. The method according to claim 21, wherein the graphical characteristic is a number of icons and the first display scale associates a particular number of icons of the graphical characteristic with the N units of the metric.

27. The method according to claim 21, wherein the metric is selected from the group consisting of: step count, heart rate, distance traveled, activity level, altitude increase, floors gained, and calories burned.

28. The method according to claim 21, wherein the circular path represents a sixty minute time interval.

29. The method according to claim 21, wherein a length of the first segment increments according to a measurement of current time.

30. The method according to claim 21, wherein the circular path represents a predetermined time period and a length of the first segment relative to a length of the circular path represents a proportion of the predetermined time period that has passed based on a current time.

31. A device, comprising:
one or more processors;
a memory; and
program code, wherein the program code is stored in the memory and configured to be executed by the one or more processors, the program code including instructions that, when executed, cause the one or more processors to:
receive first data indicative of activity of a user performed during a first time interval;
determine one or more first values of a metric based on the first data;
determine a first display scale based on the one or more first values of the metric, the first display scale associating N units of the metric with a first value of a graphical characteristic;

receive second data indicative of activity of the user performed during a second time interval having a predetermined start time and occurring after the first time interval;

determine a plurality of second values of the metric based on the second data;

determine, based on the second values of the metric and on the first display scale, corresponding second values of the graphical characteristic;

generate a first graphical indicator for each second value of the metric, each first graphical indicator exhibiting the corresponding second value of the graphical characteristic; and transmit data representing each first graphical indicator and information indicating a corresponding position at which to display each first graphical indicator on a display device, where the corresponding position of each first graphical indicator indicates a time within the second time interval associated with the corresponding second value of the metric, each of the positions corresponding with one of the first graphical indicators is arranged along a first segment of a circular path, and the first segment represents the second time interval.

32. The device according to claim 31, the program code further including instructions that, when executed, cause the one or more processors to:
determine that a predetermined time period has elapsed since determination of the first display scale; and
determine, in response to the determination that the predetermined time period has elapsed, a second display scale associating M units of the metric with the first value of the graphical characteristic.

33. The device according to claim 32, the program code further including instructions that, when executed, cause the one or more processors to:
receive third data indicative of activity of the user performed during a third time interval occurring after the second display scale is determined;
determine a plurality of third values of the metric based on the third data;
determine, based on the third values of the metric and on the second display scale, corresponding third values of the graphical characteristic;
generate a second graphical indicator for each third value of the metric, each second graphical indicator exhibiting the corresponding third value of the graphical characteristic; and
transmit data representing each second graphical indicator of the second graphical indicators and information indicating a corresponding position at which to display each second graphical indicator on the display device, where the corresponding position of each second graphical indicator indicates a time within the third time interval associated with the corresponding third value of the metric, each of the positions corresponding with one of the second graphical indicators is arranged along a second segment of the circular path, and the second segment represents the third time interval.

34. The device according to claim 33, wherein the positions on the display corresponding with the first graphical indicators and the second graphical indicators correspond with minute positions on a clock face.

35. The device according to claim 31, wherein the graphical characteristic is a length and the first display scale associates a particular length of the graphical characteristic with the N units of the metric.

36. The device according to claim 31, wherein the graphical characteristic is a number of icons and the first display scale associates a particular number of icons of the graphical characteristic with the N units of the metric.

37. The device according to claim 31, wherein the metric is selected from the group consisting of: step count, heart rate, distance traveled, activity level, altitude increase, floors gained, and calories burned.

38. The device according to claim 31, wherein the circular path represents a sixty minute time interval.

39. The device according to claim 31, wherein the length of the first segment increments according to a measurement of current time.

40. The device according to claim 31, wherein the circular path represents a predetermined time period and a length of the first segment relative to a length of the circular path represents a proportion of the predetermined time period that has passed based on a current time.

\* \* \* \* \*